United States Patent
Jetten et al.

(10) Patent No.: US 6,831,173 B1
(45) Date of Patent: Dec. 14, 2004

(54) PROCESS FOR SELECTIVE OXIDATION OF PRIMARY ALCOHOLS AND NOVEL CARBOHYDRATE ALDEHYDES

(75) Inventors: Jan Matthijs Jetten, Zeist (NL); Ronald Tako Marinus Van Den Dool, Culemborg (NL); Wim Van Hartingsveldt, Amersfoort (NL); Mario Tarcisius Raymundus Van Wandelen, Zeist (NL)

(73) Assignee: Nederlandse Organisatie voor Toegepast-Natuurwetenschappelijk Onderzoek TNO, Delft (NL)

( * ) Notice: Subject to any disclaimer, the term of this patent is extended or adjusted under 35 U.S.C. 154(b) by 0 days.

(21) Appl. No.: 09/914,182

(22) PCT Filed: Feb. 24, 2000

(86) PCT No.: PCT/NL00/00117

§ 371 (c)(1),
(2), (4) Date: Nov. 26, 2001

(87) PCT Pub. No.: WO00/50621

PCT Pub. Date: Aug. 31, 2000

(30) Foreign Application Priority Data

Feb. 24, 1999 (EP) ............................................ 99200536

(51) Int. Cl.[7] .......................... C07H 1/00; C07H 15/00; C07G 17/00
(52) U.S. Cl. ................... 536/123.1; 536/18.5; 536/105; 536/123.12; 536/124; 435/28; 435/101
(58) Field of Search ................................. 536/18, 123.1, 536/123.2, 124, 105; 435/101, 28

(56) References Cited

U.S. PATENT DOCUMENTS 3,632,802 A * 1/1972 BeMiller et al.
5,747,658 A 5/1998 Veelaert et al.

FOREIGN PATENT DOCUMENTS

WO  99/23117  5/1999
WO  WO 99/23117  * 5/1999

OTHER PUBLICATIONS

M.F. Semmelhack et al., "Oxidation of Alcohols to Aldehydes with Oxygen and Cupric Ion, Mediated by Nitrosonium Ion," *J. Am. Chem. Soc.*, V. 106, 1984, pp. 3374–3376.
James M. Bobbit et al., "Organic Nitrosonium Salts as Oxidants in Organic Chemistry," *Heterocycles*, V. 27, No. 2, 1988, pp. 509–533.
A.E.J. de Nooy et al., "Highly Selective Tempo Mediated Oxidation of Primary Alcohol Groups in Polysaccharides," *Recueil des Travaux Chimiques des Pays–Bas*, V. 113, 1994, pp. 165–166.
Arjan E.J. de Nooy et al., "On the Use of Stable Organic Nitroxyl Radicals for the Oxidation of Primary and Secondary Alcohols," *Synthesis*, 1996, pp. 1153–1174.
Philip Luner et al., "The Effect of Chemical Modification on the Mechanical Properties of Paper," *Tappi*, V. 50, 1967, pp. 37–39.
Raymond A. Young, "Bonding of Oxidized Cellulose Fibers and Interaction with Wet Strength Agents," *Wood and Fiber*, V. 10, 1978, pp. 112–119.

* cited by examiner

*Primary Examiner*—James O. Wilson
*Assistant Examiner*—Traviss C. McIntosh, III
(74) *Attorney, Agent, or Firm*—Young & Thompson

(57) ABSTRACT

A process for producing aldehydes, and/or carboxylic acids is described, in which a primary alcohol, especially a carbohydrate, is oxidized using a catalytic amount of a nitrosonium compound obtained by oxidizing a nitroxyl compound in the presence of an enzyme compound capable of oxidation. Further described are oxidized carbohydrates containing at least 1 cyclic monosaccharide chain group carrying a carbaldehyde group per 25 monosaccharide units and per molecule.

11 Claims, No Drawings

PROCESS FOR SELECTIVE OXIDATION OF PRIMARY ALCOHOLS AND NOVEL CARBOHYDRATE ALDEHYDES

The invention relates to the production of nitrosonium ions (oxoammonium ions) by oxidation of nitroxyl radicals, especially 2,2,6,6-tetramethylpiperidin-1-oxyl (TEMPO). The nitrosonium ions can be used as a catalytic oxidising agent for the selective oxidation of primary alcohols to aldehydes.

Such a process in which TEMPO is reoxidised by chemical means is known from a review by De Nooy in *Synthesis* 1996, 1153–1174 and from WO 95/07303.

It was found according to the invention that oxidation of alcohol functions, especially primary alcohol functions, can be carried out without using chlorine-based oxidising agents and with the use of hydrogen peroxide or oxygen as the ultimate oxidising agent. The oxidation according to the invention is performed using enzymes and/or metal complexes. This oxidation, when carried out on primary alcohols, surprisingly results in formation of aldehydes, if desired without substantial further oxidation to carboxylic groups using appropriate conditions. The aldehydes may be present in the (hemi)acetal form and related structures. An adaptation of the oxidation process of the invention can be used to oxidise secondary alcohols, especially carbohydrates, to keto derivatives. The process of the invention is further defined by the characterising features of the appending claims.

The non-prepublished International patent applications WO 99/23117 and WO 99/23240 describe the oxidation of cellulose or starch, respectively, using an oxidative enzyme such as laccase with oxygen and TEMPO mediation. The laccase/TEMPO oxidation of cellulose resulted in the presence of a low and unspecified level carboxyl and carbonyl groups, while the laccase/TEMPO oxidation of starch was reported to yield a product having 1 carboxyl group and 3 aldehyde groups per 100 glucose units; no method of determining aldehyde content was given.

In the following description, reference is made to TEMPO only for the sake of simplicity, but it should be understood that other suitable nitroxyls, i.e. organic nitroxyl compounds lacking α-hydrogen atoms, such as 2,2,5,5-tetramethylpyrrolidine-N-oxyl (PROXYL), 4-hydroxy-TEMPO, 4-acetamido-TEMPO and derivatives thereof and those described in WO 95/07303 can be substituted for TEMPO. These di-tert-allyl nitroxyls are especially suitable for selectively oxidising primary alcohols to aldehyde functions, in particular in the presence of secondary alcohol functions that should not be oxidised. Less sterically hindered nitroxyls, such as 4,4-dimethyloxazolidine-N-oxyl (DOXYL), are suitable for preferentially oxidising secondary alcohols to keto functions, for example in the production of keto cellulose or keto starch. The active oxidising species is the nitrosonium ion (oxoammonium ion $>N^+=O$), that is produced in situ by oxidation of the corresponding hydroxylamine and nitroxyl radical. If desired, the reaction can be performed in two steps, the production of the nitrosonium ion being the first and the oxidation of the alcohol function being the second.

A catalytic amount of nitroxyl is preferably 0.1–25% by weight, based on the primary alcohol, or 0.1–25 mol % with respect to the primary alcohol. The nitroxyl may also be immobilised, e.g. by coupling of the hydroxyl group of 4-hydroxy-TEMPO to a suitable carrier, or in the form of a polymeric nitroxyl such as:
—[$(CH_3)_2$C—NO.—C$(CH_3)_2$—A—]$_n$—, wherein A may be an alkylene group and/or a heteroatom, and n is a number form e.g. 10 up to several hundreds.

The process of the invention can be used for the oxidation of primary alcohols initially to the corresponding aldehydes. If required the primary products can be further oxidised to the corresponding carboxylic acids by using known oxidising agents such as hypochlorite, chlorite, hydrogen peroxide or by using TEMPO-mediated oxidation under more vigorous conditions such as an increased temperature e.g. from 40–80° C., or for prolonged exposure to the reaction conditions. Alternatively, the aldehyde/carboxylic acid ratio can be increased by using relative low pH's (e.g. pH 3–7), by controlled addition of oxidising agent, by lowering the oxygen concentration, or by first preparing the nitrosonium ion solution (two-step process).

The present process is especially favourable for the selective oxidation of primary hydroxyl groups in alcohols having a secondary alcohol function in addition to the primary alcohol, such as 1,6-octanediol, 1,9-octadecanediol, steroid hormones, sugar alcohols, glycosides (flavour precursors), and in particular carbohydrates having primary alcohol functions. The carbohydrates may be monosaccharides, such as glucose, fructose, disaccharides, such as sucrose, maltose, lactose, oligosaccharides and polysaccharides. The oligo- and polysaccharides may be of any type, e.g. glucans such as starch, starch components (i.e. amylose, amylopectine, dextrins), pullulan (α-1,4-α-1,4-α-1,6-glucan), cellulose (in particular non-wood), chitin, lichenin etc., furanofructans such as inulin and levan, galactans, arabinogalactans, furanoid pentosans (xylans), (galacto)mannans (guar, locust bean gum), bacterial exopolysaccharides (EPS) and the like and derivatives of such carbohydrates, such as hydrolysates. These oligo- and polysaccharides include heterosaccharides, i.e. those which have different structural units, even if those different units themselves may not have primary hydroxyl groups such as uronic acid units, e.g. in xanthan and carbohydrates derived form algae. The carbohydrates to be oxidised according to the invention include glycosides and other protected carbohydrates. Further examples are glyconic acids, such as lactobionic acid delta-lactone, that can be oxidised to glycaric acids and the like.

A distinct group of compounds suitable for oxidation with the present process consists of hydroxyalkylated carbohydrates such as hydroxypropyl cellulose, hydroxyethyl starch or hydroxyethylinulin, which result in an alternative way for producing formylalkyl carbohydrates. Other suitable carbohydrate substrates in which at least a part of the (6-) hydroxymethyl groups are intact, include for example (2- and 3-) carboxymethyl carbohydrates.

The oxidation of carbohydrates containing primary hydroxyl groups results in the corresponding carbohydrates containing aldehydes and, if desired, to carboxylic acids, with intact ring systems. Examples include α-1,4-glucan6-aldehydes, β-1,4-glucan-6-aldehydes, β-2,1-fructan6-aldehydes and β-2,6-fructan-1-aldehydes. These products are useful intermediates for functional carbohydrates wherein the aldehyde groups are further reacted with e.g. amine compounds and the like. They are also useful intermediates for crosslinked carbohydrates, in which the aldehyde groups are further reacted with e.g. diamine reagents.

The catalysts to be used according to the invention are oxidoreductases or other enzymes that are capable of oxidation in the presence of a suitable redox system. Oxidoreductases, i.e. enzymes capable of oxidation without the presence of further redox systems, to be used in the process of the invention include peroxidases and oxidases, in particular polyphenol oxidases and laccase. Certain hydrolases, such as phytase and lipases, can be used when a further redox system is present such as a metal complex, e.g.

vanadate. For example, lipases are found to be effective catalysts for selective oxidation of primary alcohol functions with TEMPO/hydrogen peroxide/copper in the presence of an organic, in particular a $C_1$–$C_6$ carboxylic acid (e.g. acetic acid). Instead of complete enzymes, so-called "synzymes", i.e. transition metal complexes mimicking enzymes can be used. Such complexes comprise e.g. vanadium, manganese, iron, cobalt, nickel or copper with complexing agents, in particular polyamines, such as 2,2'-bipyridyl, phenanthroline, tetramethylethylenediamine, pentamethyldiethylenetriamine and their cyclic counterparts such as 1,4,7-trimethyl-1,4,7-triazonane, and histidine and its oligomers. The metal-assisted enzymes require hydrogen peroxide, alkyl and ar(alk)yl hydroperoxides (such as tert-butyl hydroperoxide) or chlorite as an ultimate electron acceptor.

Peroxidases (EC 1.11.1.1–1.11.1.11) that can be used according to the invention include the peroxidases which are cofactor-independent, in particular the classical peroxidases (EC 1.11.1.7). Peroxidases can be derived from any source, including plants, bacteria, filamentous and other fungi and yeasts. Examples are horseradish peroxidase, soy-hull peroxidase, myeloperoxidase, lactoperoxidase, *Arthromyces* and *Coprinus* peroxidases. Several peroxidases are commercially available. The peroxidases require hydrogen peroxide as an electron acceptor.

Polyphenol oxidases (EC 1.10.3.1) include tyrosinases and catechol oxidases, such as lignine peroxidase. Suitable polyphenol oxidases may be obtained from fungi, plants or animals. The polyphenol oxidases require oxygen as an electron acceptor. Laccases (EC 1.10.3.2) are sometimes grouped under the polyphenol oxidases, but they can also be classified as a distinct group, sometimes referred to as p-diphenol oxidases. Laccases can be derived from plant sources or from microbial, especially fungal, sources, e.g. of the species *Trametes versicolor*. The use of recombinant laccases can be advantageous. The laccases also require oxygen as an electron acceptor.

The process of the invention can be performed under relatively mild conditions, e.g. at a pH between 2 and 10, and at a temperature between 15 and 60° C. (both depending on the particular enzyme or metal complex). The reaction medium can be an aqueous medium, or a homogeneous mixed medium, e.g. of an alcohol/water or an ether/water mixture, or a heterogeneous medium, e.g. a mixture of water and a water-immiscible organic solvent such as a hydrophobic ether, a hydrocarbon or a halogenated hydrocarbon. In the latter case, the enzyme and/or the nitroxyl and the oxidising agent may be present in the aqueous phase and the alcohol substrate and the aldehyde or ketone product may be present in the organic phase. If necessary, a phase transfer catalyst may be used. This type of reaction is suitable e.g. for the oxidation of steroids, such as the selective oxidation of 19-hydroxy steroids, and the introduction of aldehyde and/or carboxylic groups into other sensitive compounds such as flavour compounds. The reaction medium can also be a solid/liquid mixture, in particular when the enzyme of the nitroxyl are immobilised on a solid carrier. A heterogeneous reaction medium may be advantageous when the substrate or the product is relatively sensitive or when separation of the product from the other reagents may present difficulties.

The invention also pertains to novel carbohydrate oxidation products and derivatives thereof obtainable with the process of the invention. These include poly-saccharides in which at least 1 hydroxymethyl per 100, especially per 50 or even per 25, monosaccharide units has been converted to a carbaldehyde group, whether or not in hemiacetal or similar form, with the proviso that on average each molecule contains at least 1 carbaldehyde group other than a possible (hemiacetalised) aldehyde group at the reducing end of an oligo- or polysaccharide. When the carbohydrate is starch, the degree of oxidation is at least one carbaldehyde group per 25 anhydroglucose units. The carbaldehyde group is preferably present in chain (backbone) units, rather than in branch units. Not included in this at least carbaldehyde group per 100 (50, 25) units are carbaldehyde groups derived from terminal galactose units, which are obtainable by oxidation with galactose oxidase. The novel products include glycoside derivatives, i.e. products which, in addition to an acetalised end group have at least one carbaldehyde group obtainable by oxidation of non-galactose hydroxymethylene groups.

In the products of the invention, the monosaccharide rings that carry the carbaldehyde group are largely intact, and the number of aldehyde groups is greater, especially more than two times greater, than the number of carboxyl groups (other than introduced carboxyalkyl groups). Such products are not easily produce by prior art oxidation methods, which invariably lead to at least partial further oxidation to carboxyl groups. The only common carbohydrate derivatives having a predominant content of aldehyde groups are periodate-type oxidation products of starch, cellulose and the like, in which the rings bearing the aldehyde groups are broken. The aldehyde carbohydrates covered by the present invention are in particular of the non-cellulose type. The products obtainable according to the invention may contain, in addition to the aldehyde groups, other functional groups, especially carboxyl groups obtained by further oxidation or by carboxyalkylation (e.g. reaction with chloroacetic acid).

The novel derivatives of the invention are very suitable as thickeners, viscosifiers, stabilisers for emulsions and the like, and especially as starting materials for further functionalisation, especially with alcohols, amines, and other agents capable of coupling with an aldehyde function. Such agents include crosslinking agents (diamines, diols and the like), which can be used to crosslink the carbohydrates or to couple them to amino acids, proteins, active groups etc.

The process of the invention can also advantageously be used for modifying biopolymers such as starch or cotton cellulose, to allow derivatisation (e.g. dyeing of textile, strengthening of textile fibres and anti-pilling) or to adapt viscosity and other physical or chemical properties, for example to modify dietary fibres including fructans, mannans, cellulose etc.

The invention also pertains to derivatives obtained by coupling of the aldehyde carbohydrates described above with e.g. amines, especially by reductive amination, to produce imino or amino derivatives of carbohydrates as defined in the appending claims. Also, the aldehyde carbohydrates can be reacted acetalised with hydroxy-functionalised compounds, e.g. glycolic acid, for further derivatisation.

EXAMPLES

General

Uronic acid (6-COOH of hexopyranose units) contents were determined using the Blumenkrantz et al. method (*Anal. Biochem.* (1973) 54, 484), using boric acid (0.0125 M) in concentrated sulphuric acid, adding 3-hydroxybiphenyl and measuring the extinction is measured at 520 nm.

Aldehyde contents were determined either by a subtractive method (determining the uronic acid content before and after of oxidation of aldehydes with chlorite and hydrogen peroxide), or by addition of hydroxylamine hydrochloride to produce an oxime and back-titration of liberated hydrochloric acid, or by $^{13}$C NMR spectroscopy (intensity of C6 signal of aldehyde with respect to C1 of anhydroglucose unit, or intensity of C6 (C=N) in the oxime).

Example 1

Production of 6-Aldehyde Starch Using Horse Radish Peroxidase

Two grams of starch were gelatinised in 100 ml of water at 100° C. The solution obtained was cooled to 22° C. To this solution were added 25 mg TEMPO (0.13 mmol) and 40 mg of peroxidase (HRPO). The pH was adjusted to 5 with acetic acid (0.1 M). A hydrogen peroxide solution (1.5 ml 30% in 50 ml) was added drop-wise (2 ml per h). No pH adjustment was necessary. After 25 h a sample was analysed by addition of hydroxylammonium chloride. According to this indirect analysis, 30% of C6-aldehyde starch was formed, which was confirmed by $^{13}$C NMR.

Example 2

Oxidation of Pullulan with Laccase

Through a solution of 1.84 g of pullulan (11.5 mmol anhydroglucose units) 17 mg of *Trametes versicolor* laccase VIIIb (expressed in recombinant *E coli*, Wacker Chemie) and 25 mg of TEMPO in 100 ml water, oxygen gas was bubbled. The pH of the solution (6.1) decreased gradually to 4.5 after 24 hours. The aldehyde content of the solution determined by reaction with hydroxylamine hydrochloride was 1.1 mmol. The uronic acid content was 24%. To oxidise the aldehyde groups to carboxylic acid groups, the solution was treated with sodium chlorite and hydrogen peroxide. After treatment the uronic acid was increased to 32%. Based on the oxidisable groups the yields are 36 and 48%, respectively. The solution was poured out into ethanol. A white precipitate was formed, which after one day was collected by filtration and dried in vacuum. The uronic acid content of this material was 25%.

Example 3

Oxidation of Pullulan with Laccase

A solution of 1.84 g pullulan (11.5 mmol), 100 mg 4-acetamido-TEMPO, and 18 mg laccase (*T. versicolor*) was prepared. The mixture was buffered with sodium acetate/acetic acid buffer (0.05M). The initial pH of the solution was 6.1. This mixture was exposed to oxygen gas in a closed system. After one day reaction 24 ml of oxygen was consumed. To bring the pH to its original value 2 ml 0.5 M NaOH was added. The reaction was continued for another day, resulting in the consumption of 20 ml of oxygen gas. The final pH was 5.1. The pH was adjusted again by addition of 1.2 ml NaOH (0.5 M). 15 mg laccase was added and the reaction was allowed to proceed for two days. After this period the pH was 4.5 and 30 ml oxygen gas was consumed. To bring the pH to 6, 3 ml 0.5 NaOH had to be added. To the solution 0.2 ml hydrogen peroxide (30% w/w) and 250 mg sodium chlorite were added. After one day reaction the uronic acid content was measured. The yield of uronic acid before oxidation with sodium chlorite was 550 mg (26%) and after 695 mg (33%).

Example 4

Preparation of the Nitrosonium Salt of TEMPO Using Laccase

A solution of TEMPO nitrosonium ion was made with laccase as follow. 6.9 g TEMPO was dissolved in 1 l demi water. 200 mg laccase VIIIb from *T. versicolor* (Wacker) was suspended in 20 ml demi water. After stirring the enzyme solution for 10 minutes, the supernatant after centrifugation (5 min 1500×g) was desalted using a P6 column. The desalted material was added to the TEMPO solution. In approximately 150 minutes under pH stat conditions at pH 5, ambient temperature, aerated with air sparge, 91% of the TEMPO was converted to nitrosonium, as determined by the consumption of 100.8 ml of HCl (0,4 N) and a shift from a yellow to a more orange colour (the ratio E480/E430 increases from approximately 0.3 to 1).

Example 5

Oxidation of Starch Using Nitrosonium Salt and a UF Membrane System

The nitrosonium solution obtained according to example 4 was buffered with 0.2 M acetate at pH 4.5. 2 g native potato starch was gelatinised in 100 ml water and mixed with 100 ml of the buffered nitrosonium solution. The mixture was poured into a 200 ml stirred UF vessel (cut-off 5 kD). Approximately 800 ml of the nitrosonium solution was pumped into the vessel at a rate of 0.5 ml/min. at room temp 20° C. The permeate indicated a conversion of 50% of the nitrosonium ion bake to TEMPO (based on the E480/E430 ratio). After this treatment, the uronic acid content of the starch was found to be 38%.

Example 6

Conversion of Starch Using Oxygen/Laccase/TEMPO Cycle

Starch solutions were prepared by gelatinising Lintner potato starch (Sigma S-2630) in water. The pH was adjusted by addition of 0.2 M succinic acid/succinate buffer. Tempo or 4-acetamido tempo (4acmT) was added. (TEMPO forms a precipitate with starch in some conditions, which dissolves during the process.) Laccase VIIIb from *Trametes versicolor* expressed in *E. coli* (from Wacker Chemie) was suspended at 10 mg/ml 0,2 M succinate buffer pH 6. After centrifugation (5 min 1500 g) for 10 mg laccase 1 ml of the supernatant was added. The oxygen transfer to the solution was enhanced in stirred pressurised vessels A en B. Both vessels contained approximately 100 ml. The area of contact with the gas phase was 70 cm$^2$ for vessel A and 32 cm$^2$ for vessel B. The experimental conditions and the results with regard to $C_6$-oxidation (aldehyde or carboxylic acid) are summarised in tables 1 and 2. Important parameters for the reaction conditions are:

oxygen transfer to the solution, pH, temperature, concentration of TEMPO, enzyme and starch.

The formation of uronic acids was monitored according to Blumenkrantz. The formation of aldehydes was monitored after oxidation to uronic acids under the following conditions:

To 5 ml sample (20 g/l starch) 0.095 ml 3% $H_2O_2$ and 0.5 ml 20 mg/ml sodium chlorite was added. The uronic acid content was measured after 16 h at room temperature.

TABLE 1-1

Summary of influences studied in vessel A

| air bar | O2 bar | Starch lintner g/l | Laccase mg/100 ml | pH | Temp o g/l | 4acmT[1] g/l | T °C. | Time h | % COOH | % ald or hemi[2] |
|---|---|---|---|---|---|---|---|---|---|---|
| 2 |   | 10 | 100 | 6 | 1 |   | 25 | 45 | 73.4 | nd |
| 1.5 |   | 10 | 100 | 5 |   | 5 | 25 | 45 | 54.2 | nd |
|   | 4 | 10 | 100 | 6 | 4 |   | 30 | 15 | 94.9 | nd |
| 2 |   | 10 | 100 | 6 | 4 |   | 30 | 15 | 100.0 | nd |
|   | 1 | 10 | 100* | 5.3 |   | 6 | 30 | 15 | 78.8 | nd |
| 2 |   | 10 | 10 | 6 | 4 |   | 30 | 20 | 60.3 | 4.9 |
|   | 1 | 10 | 10* | 6 | 4 |   | 30 | 20 | 50.0 | 5.1 |
|   | 4 | 10 | 10 | 5.3 |   | 4 | 30 | 20 | 30.5 | 11.9 |
|   | 4 | 20 | 10* | 4.5 |   | 4 | 30 | 20 | 19.7 | 12.0 |
| 2 |   | 20 | 10 | 4 |   | 4 | 30 | 20 | 11.5 | 12.5 |

*the enzyme was pumped into the vessel during 20 h
[1]4acmT = 4-acetamido-TEMPO
[2]aldehyde or hemiacetal thereof

TABLE 1-2

Summary of influences studied in vessel B

| O2 bar | Starch lintner g/l | laccase mg/100 ml | pH | Temp o g/l | 4acmT g/l | T °C. | time h | % COOH | % ald or hemi |
|---|---|---|---|---|---|---|---|---|---|
| 4 | 10 | 100 | 6 | 4 |   | 30 | 15 | 94.9 | nd |
| 4 | 10 | 10 | 5.3 |   | 4 | 30 | 20 | 30.5 | 11.9 |
| 6 | 20 | 1 | 6 |   | 4 | 40 | 20 | 7.1 | 4.2 |

Example 7

Oxidation of Pullulan by TEMPO/Mn/$H_2O_2$

In 25 ml of water 250 mg pullulan and 20 mg of TEMPO were dissolved. To this solution 25 mg manganese nitrate was added, followed by 100 μl of hydrogen peroxide (3% solution, w/w) and bipyridine solution (5 ml 0.05 M). The reaction was conducted at pH 6.5. At the first day 60 mg (1.8 mmol) hydrogen peroxide was added and after one day 25 mg of uronic acid was formed. During the second day 30 mg hydrogen peroxide was added and the amount of uronic acid was increased to 50 mg. The aldehyde groups were converted into carboxylic acid groups with hydrogen peroxide/sodium chlorite the content raised to 90 mg. (D.O. 60%).

What is claimed is:

1. A process for oxidizing a polysaccharide selected from the group consisting of alpha-glucans, mannans, galactans, and fructans, comprising reacting said polysaccharide with an oxidizing agent selected from the group consisting of oxygen, hydrogen peroxide, alkyl, aryl and aralkyl hydroperoxides and chlorite, in the presence of a nitroxyl compound and in the presence of an enzyme capable of oxidation, in an aqueous medium, or in a mixture of water with an alcohol, an ether or a water-immiscible organic solvent.

2. The process according to claim 1, wherein the nitroxyl compound is a di-tert-nitroxyl compound.

3. The process according to claim 1, wherein the enzyme capable of oxidation is an oxidoreductase.

4. The process according to claim 3, wherein the enzyme is a peroxidase, and the oxidizing agent is hydrogen peroxide.

5. The process according to claim 3, wherein the enzyme is a polyphenol oxidase or a laccase and the oxidizing agent is oxygen.

6. The process according to claim 1, wherein the enzyme is a phytase or lipase.

7. The process according to claim 1, comprising oxidizing said carbohydrate to obtain a carbonyl-containing carbohydrate containing at least one cyclic monosaccharide chain group carrying a carbaldehyde group per 25 monosaccharide units and per molecule.

8. The process according to claim 2, wherein said di-tert-nitroxyl compound is 2,2,6,6-tetramethylpiperidin-1-oxyl (TEMPO).

9. The process according to claim 4, wherein said peroxidase is horse radish, soy-bean, lignin peroxidase or myelo- or lacto-peroxidase.

10. An oxidized carbohydrate, wherein said carbohydrate is selected from the group consisting of polysaccharides of alpha-glucan, mannan, galactan, fructan, and chitin types, and carbohydrate glycosides, containing 2 to 50 cyclic monosaccharide groups carrying a carbaldehyde group per 50 monosaccharide units and per molecule, or a carboxyalkyl derivative thereof.

11. The oxidized carbohydrate according to claim 10, containing at least 5 monosaccharide units per molecule.

* * * * *